United States Patent [19]

Fields et al.

[11] 3,976,674

[45] Aug. 24, 1976

[54] ALUMINUM SALTS OF SUBSTITUTED PHENYLALKANOIC ACIDS

[75] Inventors: Calvin H. Fields; Clarence A. Hirsch, both of Indianapolis, Ind.

[73] Assignee: Eli Lilly and Company, Indianapolis, Ind.

[22] Filed: May 13, 1974

[21] Appl. No.: 469,257

Related U.S. Application Data

[63] Continuation-in-part of Ser. No. 302,709, Nov. 1, 1972, abandoned.

[52] U.S. Cl. .............................. 260/448 R; 424/317
[51] Int. Cl.² ........................................... C07F 5/06
[58] Field of Search ................................ 260/448 R

[56] References Cited

UNITED STATES PATENTS

| 3,517,051 | 6/1970 | Bolhofer | 260/448 R X |
| 3,600,437 | 8/1971 | Marshall | 260/448 R X |

*Primary Examiner*—Helen M. S. Sneed
*Attorney, Agent, or Firm*—Ralph W. Ernsberger; Everet F. Smith

[57] ABSTRACT

Novel Mono- and di-basic aluminum salts of 2-(3-phenoxyphenyl)- and 2-(3-phenylthiophenyl)alkanoic acids provide tasteless and practically water insoluble forms of said alkanoic acids, which have anti-inflammatory activity in mammals, for formulating pharmaceutical suspensions.

5 Claims, No Drawings

ALUMINUM SALTS OF SUBSTITUTED PHENYLALKANOIC ACIDS

CROSS-REFERENCE

This is a continuation-in-part of patent Application Ser. No. 302,709, filed Nov. 1, 1972, now abandoned.

BACKGROUND OF THE INVENTION

1. Field of the Invention

This invention relates to tasteless and practically water insoluble salts, useful in formulating pharmaceutical suspensions, of physiologically active substituted phenylalkanoic acids. More particularly, this invention relates to the mono- and di-basic aluminum salts of 2-(3-phenoxyphenyl)-and 2-(3-phenylthiophenyl)alkanoic acids. Said salts, being tasteless and practically water insoluble at pH's of from about 6 to 9, and which revert to the physiologically active phenylalkanoic acid moieties at the pH of the stomach, are uniquely adapted for use in pharmaceutical suspension.

2. Description of the Prior Art

Physiologically active substituted phenylalkanoic acids are taught and claimed in U.S. Pat. No. 3,600,437. The substituted phenylalkanoic acids there taught are particularly active as antiinflammatory agents.

Antiinflammatory agents are almost uniformly prescribed in most clinical cases of arthritis. And, generally, arthritis is an affliction of the older segment of the population. In those persons 70 and older, almost every one has an active case of clinically diagnosed arthritis. Solid pharmaceutical dosage forms for oral administration, such as capsules, granules, pills, powders, and tablets can be readily prepared directly from the more soluble salts of substituted phenylalkanoic acids. However, many older persons prefer liquid medical preparations to the solid forms, because such are easier to swallow.

Most salts of substituted phenylalkanoic acids having antiinflammatory activity are difficult to formulate into pharmaceutically acceptable liquid dosage form because of a small amount of water solubility which makes the taste hard to mask.

Accordingly it is an object of this invention to provide water insoluble salts of the substituted phenylalkanoic acids.

It is a further object of this invention to provide water insoluble salts of the substituted phenylalkanoic acids which are biologically available when ingested into the stomach of a mammal.

It is yet another object of this invention to provide biologically available water insoluble salts of the substituted phenylalkanoic acids which are chemically stable and inert toward the commonly used adjuvants employed in pharmaceutical suspension.

Still another object of the instant invention is to provide chemically stable, inert, water insoluble, and biologically available salts of the substituted phenylalkanoic acids which are tasteless.

A further object of this invention is to provide chemically and physically stable pharmaceutical suspensions of the substituted phenylalkanoic acids.

SUMMARY

It has now been discovered that the mono- and di-basic aluminum salts of substituted phenylalkanoic acids having antiinflammatory activity are practically water insoluble, tasteless, unreactive towards commonly employed pharmaceutical suspension adjuvants, chemically stable at a pH of from about 6.0 to 9.0, and adapted for formulating into exceptionally elegant pharmaceutical suspensions. Such salts are prepared by reacting an alkali metal salt of the substituted phenylalkanoic acid with a water soluble aluminum salt such as aluminum chloride hexahydrate or aluminum nitrate nonahydrate, which can be adjusted to produce either the mono- or di- basic salt or by directly reacting the substituted phenylalkanoic acid with a dispersion of aluminum hydroxide gel in water.

Pharmaceutical suspensions are prepared by grinding the desired aluminum salt to a powder having a mesh size below 200 (U.S. screen) and adding the resulting finely divided powder to a vehicle adjusted to an appropriate specific gravity and viscosity with commonly utilized pharmaceutical suspension adjuvants.

DESCRIPTION OF THE PREFERRED EMBODIMENTS

In one aspect of the instant invention, 3-phenoxyphenyl and 3-phenylthiophenyl alkanoic acids are combined with aluminum in salts represented by the following formula:

wherein:
$n$ is 1 or 2; and
$R_1$ is the moiety

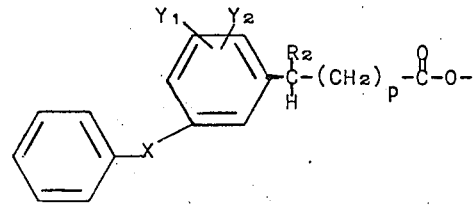

wherein:
$p$ is an integer from 0 to 3;
X is oxygen or sulfur;
$R_2$ is hydrogen, $C_1$-$C_5$ alkyl, $C_2$-$C_5$ alkenyl, $C_2$-$C_5$ alkynyl, or $C_3$-$C_6$ cycloalkyl;
and
$Y_1$ and $Y_2$ are independently, hydrogen, hydroxy, halo, $C_1$-$C_3$ alkyl, or $C_1$-$C_3$ alkyl, or $C_1$-$C_3$ alkoxy, but $Y_2$ is hydrogen when $Y_1$ is hydroxy or $C_1$-$C_3$ alkoxy.

This invention relates to both the mono- and di- basic aluminum salts of the phenylalkanoic acid compounds described above. The term "monobasic" refers to the aluminum salt which has one hydroxyl (OH) substituent bonded to the aluminum. The term "dibasic" refers to the aluminum salt which has two hydroxyl (OH) substituents bonded to the aluminum.

In the description of the substituents present in the formula described above, the terms have the following meanings:

"Halo" includes chloro, fluoro, bromo, and iodo.

"$C_1$-$C_3$ alkyl" includes methyl, ethyl, n-propyl and isopropyl.

"C₁-C₅ alkyl" refers to methyl, ethyl, n-propyl, isopropyl, n-butyl, sec-butyl, isobutyl, t-butyl, isoamyl, neopentyl, and the like.

"$C_2$-$C_5$ alkenyl" refers to the $C_2$-$C_5$ alkyl group, as defined above, from which a hydrogen atom has been removed from each of two adjacent carbon atoms to produce ethylenic unsaturation; e.g., vinyl, allyl, methallyl, 1-pentenyl, and the like.

"$C_2$-$C_5$ alkynyl" refers to the $C_2$-$C_5$ alkyl groups, as defined above, from which two hydrogen atoms have been removed from each of two adjacent carbon atoms to produce acetylenic unsaturation; e.g., ethynyl, propargyl, 2-butynyl, 1-pentynyl, and the like.

"$C_3$-$C_6$ cycloalkyl" includes cyclopropyl, cyclobutyl, cyclopentyl and cyclohexyl.

"$C_1$-$C_3$ alkoxy" includes methoxy, ethoxy, propoxy, and isopropoxy.

The 3-phenoxyphenyl- and 3-phenylthiophenylalkanoic acid moieties of the useful compounds of this invention are excellent anti-inflammatory agents. U.S. Pat. No. 3,600,437 describes the useful anti-inflammatory activity of said alkanoic acid compounds. Methods for the preparation of representative members of this class of compounds are exemplified in the aforementioned patent.

The novel compounds represented by the formula set forth above have anti-inflammatory activity similar to the anti-inflammatory activity of the alkanoic acid moiety standing alone. And these useful compounds have the surprising additional useful property of tastelessness.

This useful property of tastelessness, coupled with the almost total lack of solubility-in-water associated with the aluminum salts of the physiologically active phenylalkanoic acids, provide compounds which can be incorporated into suspensions possessing outstanding pharmaceutical elegance. In these salts, there can be either one or two of the physiologically active phenylalkanoic acid moieties in each molecule. In either case, the compounds can be formulated into pharmaceutical suspensions having excellent stability. And, upon ingestion into the acid environment of the stomach of a mammal, including humans, the phenylalkanoic acid moieties are disassociated from the salts and revert to the 2-(3-phenoxyphenyl)- or 2-(3-phenylthiophenyl)-alkanoic acid compounds. As such, they are assimilated from the gastro-intestinal tract and become biologically available to effect an anti-inflammatory activity.

It should be understood that both the *d* and *l* isomers of the α-alkyl compounds which are substituents on the aluminum hydroxides are contemplated with the scope of this invention. Moreover, the racemic mixtures of the *d* and *l* isomers are embraced herein, inasmuch as both the *d* and *l* isomers have been found to have substantially identical activity.

Representative compounds of the present invention include the following:

2-Cyclopropyl-2-(2,5-dichloro-3-phenoxyphenyl)-acetoxy aluminum dihydroxide
di-[2-(3-phenoxyphenyl)acetoxy] aluminum hydroxide.
2-(4-nitro-3-phenoxyphenyl)acetoxy aluminum dihydroxide
di-[2-(4-methoxy-3-phenoxyphenyl)acetoxy] aluminum hydroxide
l-2-(3-phenoxyphenyl)acetoxy aluminum dihydroxide
di-[2-(2-iodo-5-phenylthiophenyl)acetoxy] aluminum hydroxide
2-(2-methyl-5-phenoxyphenyl)acetoxy aluminum dihydroxide
2-(3-phenoxyphenyl)propionoxy aluminum dihydroxide
di-[2-(3-phenoxyphenyl)propionoxy] aluminum hydroxide
di-[2-(5-propoxy-3-phenylthiophenyl)butyroxy] aluminum hydroxide
2-(5-chloro-3-phenoxyphenyl) propionoxy aluminum dihydroxide
di-[2-cyclopropyl-2-(3-phenoxyphenyl)acetoxy] aluminum hydroxide
2-Cyclohexyl-2-(3-phenoxyphenyl)acetoxy aluminum dihydroxide
di-[2-vinyl-2-(4chloro-3-phenylthiophenyl)acetoxy] aluminum hydroxide
2-(2,5-dimethyl-3-phenylthiophenyl)acetoxy aluminum dihydroxide
di[2-(2-fluoro-5-ethyl-3-phenoxyphenyl)acetoxy] aluminum hydroxide
2-(4-ethoxy-3-phenoxyphenyl)propionoxy aluminum dihydroxide
di-[d-2-(3-phenylthiophenyl)propionoxy] aluminum hydroxide
2-(3-phenylthiophenyl)butyroxy aluminum dihydroxide
di-[2-(3-phenylthiophenyl)valeroxy] aluminum hydroxide
2-(4-chloro-3-phenylthiophenyl)propionoxy aluminum dihydroxide
di-[2-(4-chloro-3-phenylthiophenyl)acetoxy] aluminum hydroxide
2-(2-methyl-5-phenylthiophenyl)acetoxy aluminum dihydroxide
di-[2-(2-fluoro-5-phenylthiophenyl)propionoxy] aluminum hydroxide
2-propargyl-2-(3-phenoxyphenyl)acetoxy aluminum dihydroxide
di-[2-(2,5-dichloro-3-phenoxyphenyl)acetoxy] aluminum hydroxide
2-(4-iodo-6-hydroxy-3-phenylthiophenyl)propionoxy aluminum dihydroxide
di-[2-(2,5-dibromo-3-phenylthiophenyl)acetoxy] aluminum hydroxide
d-2-(3-phenoxyphenyl)propionoxy aluminum dihydroxide
di-[2-(1-pentyl)-2-(3-phenoxyphenyl)acetoxy] aluminum hydroxide
2-(4-methyl-3-phenoxyphenyl)acetoxy aluminum dihydroxide
di-[2-(4-hydroxy-3-phenoxyphenyl)acetoxy] aluminum hydroxide
2-(4-chloro-3-phenoxyphenyl)propionoxy aluminum dihydroxide
di-[2-(4-chloro-3-phenoxyphenyl)acetoxy] aluminum hydroxide
2-(5-chloro-3-phenoxyphenyl)acetoxy aluminum dihydroxide
di-[2-(2-chloro-3-phenoxyphenyl)acetoxy] aluminum hydroxide
2-(2-fluoro-3-phenoxyphenyl)acetoxy aluminum dihydroxide
di-[2-(2-ethyl-3-phenoxyphenyl)propionoxy] aluminum hydroxide
2-(3-phenylthiophenyl)acetoxy aluminum dihydroxide di-[2-(3-phenylthiophenyl)propionoxy] aluminum hydroxide 2-(4-hydroxy-3-phenylthiophenyl)acetoxy aluminum dihydroxide di-[2-(4-methyl-3-phenylthiophenyl)propionoxy] aluminum hydroxide 2-(5-chloro-3-phenylthiophenyl)acetoxy aluminum dihydroxide di-[2-(2-chloro-3-phenylthiophenyl)propionoxy] aluminum hydroxide 2-(3-phenoxyphenyl)butyroxy aluminum dihydroxide di-[2-(3-phenoxyphenyl)valeroxy] aluminum hydroxide The useful compounds of this invention can be prepared by a number of different procedures. One procedure involves reacting the sodium salt of an appropriate 3-phenoxyphenyl- or 3-phenylthiophenylalkanoic acid with a water soluble aluminum salt; e.g., aluminum nitrate, or aluminum chloride. Sodium carbonate or bicarbonate is added to buffer the suspension to a pH greater than 7.0. The preparation is carried out in an aqueous medium with vigorous agitation.

A second method involves reacting an appropriate 3-phenoxyphenyl- or 3-phenylthiophenylalkanoic acid with aluminum hydroxide in a well-stirred hot aqueous suspension.

A third method, better suited for the preparation of the dibasic salt, comprises adding aluminum hydroxide gel powder to an aqueous solution of the sodium salt of an appropriate 3-phenoxyphenyl- or 3-phenylthiophenylalkanoic acid, and then slowly (4 hours) back titrating the reaction mixture with hydrochloric acid at 60°–80°C. to a pH of about 4.0 with vigorous agitation.

Still another method, which is a variation of the first, calls for the controlled addition of two aqueous solutions into a well-stirred vessel, one solution containing the aluminum ion and the other an alkali metal salt of an appropriate 3-phenoxyphenyl- or 3-phenylthiophenylakanoic acid, plus an excess of a base to neutralize the remaining anions of the reaction. The aqueous reaction medium is held at a temperature of about 50° to 65°C, preferably the latter and the pH is maintained in the 6.0 –8.0 range, preferably between 7.0 and 8.0. The dibasic aluminum salt is prepared by utilizing a final aluminum ion to acid moiety molar ratio of 1:1 and maintaining an excess of aluminum ions during the course of the reaction. The monobasic salt is prepared by utilizing a molar ratio of 1.2 aluminum ion to acid moiety and maintaining an excess of acid moiety ions during the course of the reaction. The methods are detailed in Examples 1 and 2.

EXAMPLE 1

Preparation of 2-(3-Phenoxyphenyl)propionoxy Aluminum Dihydroxide

To 100 ml. of deionized water in a suitable vessel were added 24.16 g. (0.1 mole) of 2-(3-phenoxyphenyl)propionic acid. The acid was dissolved by the addition of 20 ml. of 5N NaOH to form sodium 2-(3-phenoxyphenyl)propionate. The pH was about 9.4.

In a separate vessel, 37.5 g. (0.1 mole) of Al(NO$_3$)$_3$.9H$_2$O were dissolved in 250 ml. of deionized water. The pH was about 1.6.

In a third vessel, a three necked round bottom flask equipped with a stirrer, 16.8 g. (0.2 mole) of NaHCO$_3$ were dissolved in 200 ml. of deionized water.

The reaction forming the 2-(3-phenoxyphenyl)propionoxy aluminum dihydroxide was carried out in the third vessel by slowly adding continuously equivolumetric quantities of each of the solution of the sodium 2-(3-phenoxyphenyl)-propionate and the solution of aluminum nitrate to the sodium bicarbonate solution with continuous stirring. About 30 minutes were required to complete the addition of the two solutions to the reaction vessel as the rate of addition was controlled to minimize foaming. Stirring was continued for another 30 minutes and the resulting precipitate was filtered and washed. The filter cake was dried for 48 hours at 50°C. Twenty-eight and four-tenths grams of reaction product (94% yield) were obtained which analyzed 98.2% 2-(3-phenoxyphenyl)propionoxy aluminum dihydroxide.

EXAMPLE 2

Preparation of Di-[2-(3-Phenoxyphenyl)propionoxy] Aluminum Hydroxide

In a suitable vessel, 32.8 g. of anhydrous sodium carbonate were dissolved in 500 ml. of deionized water. To this solution were added 100 g of 2-(3-phenoxyphenyl)propionic acid. The reaction mixture was agitated vigorously until all of the acid was in solution and reacted to form sodium 2-(3-phenoxyphenyl)propionate. The resulting reaction mixture was diluted to a total volume of 2 l with deionized water. The dilute propionate solution was transferred to a 4 liter beaker.

In a separate vessel, 49.8 g of AlCl$_3$.6H$_2$O were dissolved in 200 ml. of deionized water. The aluminum chloride solution was diluted to 500 ml. total volume and placed in an addition funnel.

The reaction forming di-[2-(3-phenoxyphenyl)propionoxy] aluminum hydroxide was carried out by continuously, slowly adding the alluminum chloride solution to the propionate solution with stirring. The rate of addition was controlled to minimize foaming and required about 30 minutes. When the addition of the aluminum chloride solution was complete, the reaction mixture was slowly heated to 70° C. with stirring and then gradually cooled to 50° C. The precipate which formed was filtered, using a sintered glass filter, and the filter cake was washed with methanol. The resulting reaction product was dried at 50° C. overnight and then ground to a 200 mesh powder. One-hundred and nine grams of reaction product (99% yield) were obtained which analyzed 98.3% di-[2-(3-phenoxyphenyl)propionoxy] aluminum hydroxide.

In another aspect of this invention, the novel mono- and di-basic aluminum salts of 2-(3-phenoxyphenyl)- and 2-(3-phenylthiophenyl)alkanoic acids are formulated into pharmaceutical suspensions having exceptional palatability and stability. And when such a suspension is ingested into the acid environment of the stomach, the physiologically active moiety the phenylalkanoic acid- is disassociated from the aluminum salt and is assimilated into the blood stream of the ingester who then receives the benefit of the anti-flammatory activity of the alkanoic acid.

The useful mono- and di-basic aluminum salts of 2-(3-phenoxyphenyl)- and 2-(3-phenylthiophenyl)alkanoic acids are essentially tasteless and practically insoluble in water at pHs from near neutral to slightly alkaline; e.g., from 6.0 to 9.0. Furthermore, these novel salts are pharmaceutically compatible with a wide range of suspension adjuvants commonly employed in formulating pharmaceutical suspension.

It is desireable that physiologically active agents formulated into pharmaceutical suspensions should have a particle size below 150 mesh (U.S. screen), preferably from 200 to 325 mesh. The particle size should be small enough to impart good feel to the mouth when the suspension is taken orally. The absence of grittiness is desired. But at the same time, the particle size should not be a great deal smaller than needed, because ultra small particles tend to thicken a suspension and as a consequence reduce the practical quantity of material which can be effectively formulated into a suspension.

The useful compounds of the instant invention can be readily ground to a powder suitable for incorporation in a pharmaceutical suspension. It was found that a powder of these compounds which passes 200 mesh (U.S. screen) is admirably adapted for formulation into a suspension.

Pharmaceutical suspensions are usually prepared by employing a specific adjusting agent, such as one of the edible sugars, fructose, dextrose, mannose, lactose, sucrose, and the like, an edible polyol such as glycerin, propylene glycol, mannitol, and the like. The specific gravity adjusting agent is dissolved in water to provide a vehicle having a specific gravity just a little bit below the specific density of the physiologically active agent suspended therein. About 40 percent by weight of sucrose in water provides a suitable vehicle for suspending one of the useful compounds of the instant invention therein.

A viscosity adjusting substance is generally utilized in a pharmaceutical suspension to retard the rate of settling of the physiologically active agent. Among such substances are methyl cellulose, polyvinylpyrolidone, hydroxypropylcellulose, sodium carboxymethylcellulose, microcrystalline cellulose, and the like, finely ground bentonite, gelatin, naturally occurring gums such as guar, and the like. A particularly well adapted viscosity adjusting substance for use in preparing a suspension of the novel compounds of this invention is a combination of about 89 percent microcrystalline cellulose and 11 percent sodium caboxymethylcellulose. The combination is employed in an amount of about 2.5 percent weight/volume of the finished suspension.

A preservative, such as one of the parabens, is generally added to the suspension. Methylparaben in an amount of about 0.08 percent weight/volume of the finished suspension serves as an effective preservative of a pharmaceutical suspension of the useful compounds of this invention.

Pharmaceutical elegance is provided by employing suitable flavoring agents and colorants. Generally the color is selected to provide harmony with the flavors employed.

Typical useful pharmaceutical suspensions of both the mono- and di-basic aluminum salts of 2-(3-phenoxyphenyl)- and 2-(3-phenylthiophenyl)alkanoic acids are exemplified in Examples 3 and 4, below. The concentration of 300 mg. of alkanoic acid equivalent per 5 ml. of suspension was designed to provide one recommended dose in 5 ml. Other concentrations can be easily prepared by simply adjusting the amount of the aluminum salt of the phenylalkanoic acid that is added to the vehicle. Suspensions containing as much as 1000 mg. per 5 ml. can be easily formulated. The 5 ml. quantity of suspension was exemplified as this is the amount generally measured by one teaspoon. Other amounts can be just as easily employed to contain the desired quantity of the physiologically active agent.

EXAMPLE 3

Typical Pharmaceutical Suspension Containing 300 mg. of 2-(3-Phenoxyphenyl)propionic Acid Equivalent as 2-(3-Phenoxyphenyl)proionoxy Aluminum Dihydroxide per 5 ml. of Suspension To make 1 liter of suspension employ the formula and method of preparation that follows:

| | |
|---|---:|
| Place in suitable container calibrated to 1 liter- | |
| Water Purified | 400.00 ml. |
| Methylparaben | 0.80 g |
| Heat to 60°C. Dissolve, add- | |
| Microcrystalline Cellulose 89 percent with Sodium-Carboxymethylcellulose 11 percent | 25.00 g |
| Mix well, maintain 60°C. while mixing. | |
| Mix for 30 minutes. | |
| Let stand overnight at room temperature. | |
| Mix well, add- | |
| Sucrose Granulated Cane | 400.00 g |
| Dissolve, add- | |
| Water, Purified | 100.00 ml |
| Mix well, add slowly- | |
| 2-(3-phenoxyphenyl)propionoxy aluminum dihydroxide, 200 mesh powder | 75.00 g |
| Mix until uniform, add- | |
| (Imit. Pineapple Flavor RF1698(Rhodia) | 0.10 ml |
| (Orange Flavor Imit.59.107/A(Firmenich) | 0.10 ml |
| (Alcohol 95% | 1.80 ml |
| Mix well, add- | |
| (F D and C Yellow No. 5 | 0.40 g |
| (F D and C Yellow No. 6 | 0.02 g |
| (Water Purified | 5.00 ml. |
| Mix well, add- | |
| Water Purified q.s. to | 1000.00 ml. |
| Mix well, run through mill, mix well. | |

EXAMPLE 4

Typical Pharmaceutical Suspension Containing 300 mg. of 2-(3-Phenoxyphenyl)propionic Acid Equivalent as Di-[2-(3-Phenoxyphenyl)propionoxy] Aluminum Hydroxide per 5 ml. of Suspension Proceed as outlined in Example 3 except for 2-(3-Phenoxyphenyl)propionoxy aluminum dihydroxide, 75.0 g, substitute di-[2-(3-phenoxyphenyl)propionoxy] aluminum hydroxide, 65.22 g.

In addition to the suspension exemplified in Examples 3 and 4, a pharmaceutically elegant suspension containing di-[2-(3-phenoxyphenyl)propionoxy] aluminum hydroxide as the compound containing the physiologically active moiety, 2(3-phenoxyphenyl)propionic acid was prepared by reacting in situ the C- (acid with aluminum hydroxide in an appropriate mole ratio. The preparation of this pharmaceutical suspension comprises the steps of: A- In a suitable vessel, (1) dissolving a preservative in water, and (2) dispersing a viscosity adjusting agent in the solution from (1); B- In a separate vessel, (1) mixing aluminum hydroxide powder with water, (2) heating the mixture from (1) to 65° C., and (3) adding 2-(3-phenoxyphenyl)propionic acid slowly to the heated mixture from (2); and C-(1) adding the reaction mixture from (B) to the dispersion from (A), and (2) adding a specific gravity adjusting agent thereto. Alternatively, such an in situ suspension can be prepared by substituting an aluminum ion containing compound such as aluminum nitrate or aluminum chloride for the aluminum hydroxide powder of step B (1) and an alkali metal salt of 2-(3-phenoxyphenyl)propionic acid for the propionic acid of step B (2).

The same preservatives, viscosity adjusting substances and specific gravity adjusting agents as are illustrated above can be employed in preparing the aforementioned in situ suspension.

The in situ preparation of di-(alkanoic acid) aluminum hydroxide suspensions are examplified in Examples 5 and 6.

EXAMPLE 5

Preparation of a Pharmaceutical In Situ Suspension Containing 300 mg. of 2-(3-Phenoxyphenyl)propionic Acid Equivalent as di-[2(3-Phenoxyphenyl)propionoxy] Aluminum Hydroxide Per 5 ml. of Suspension To make 1 liter of suspension employ the formula and method of preparation that follows:

| | | |
|---|---|---|
| (A) | Place in suitable container calibrated to 1 liter- | |
| | Water Purified | 400.00 ml |
| | Methylparaben | 0.80 g |
| | Heat to 60°C., dissolve, add- | |
| | Microcrystalline Cellulose 89 percent with Sodium Carboxymethylcellulose 11 percent | 25.00 g |
| | Mix well, maintain 60°C. while mixing. | |
| | Mix for 30 minutes. | |
| | Set container aside. Let stand overnight. | |
| (B) | Place in 1500 ml. beaker- | |
| | Water Purified | 300.00 ml |
| | Aluminum Hydroxide Gel Powder | 25.34 g |
| | Mix well. Heat to 65°C., | |
| | Add through addition funnel dropwise over 1¾ hour period, maintaining 60°C. temperature- with mixing | |
| | 2-(3-Phenoxyphenyl)propionic acid | 60. g |
| | Cool to room temperature | |
| | Continue mixing | |
| (C) | Add reaction mixture from (B) to dispersion from A. | |
| | Add Sucrose granulated cane | 400. g |
| | Dissolve. Add- | |
| | (Imit.Pineapple Flavor RF1698(Rhodia) | 0.10 g |
| | (Orange Flavor Imit.59.107/A(Firmenich) | 0.10 g |
| | (Alcohol 95% | 1.80 ml |
| | Mix well. Add- | |
| | (F D and C Yellow No. 5 | 0.40 g |
| | (F D and C Yellow No. 6 | 0.02 g |
| | (Water Purified | 5.00 ml |
| | Mix well. Add- | |
| | Water Purified q.s. to | 1000.00 ml |
| | Mix well. Run through mill. Mix well. | |

EXAMPLE 6

Preparation of a Pharmaceutical In Situ Suspension Containing 100 mg. of 2-(3-Phenoxyphenyl)propionic Acid Equivalent as di[2-(3-Phenoxyphenyl)propionoxy]aluminum Hydroxide per 5 ml. of Suspension To make 2 liters of suspension employ the formula and process of preparation that follows:

| | | |
|---|---|---|
| (A) | Place in suitable container calibrated to 2 liters- | |
| | Water Purified | 400.00 ml |
| | 2-(3-Phenoxyphenyl)propionic acid | 40.00 g |
| | Sodium carbonate, anhydrous | 13.20 g |
| | Mix well to dissolve, heating to 60–65°C. | |
| (B) | Place in suitable container- | |
| | Water purified | 400.00 ml |
| | Aluminum chloride, hexahydrate | 20.00 g |
| | Mix well to dissolve, heating to 60–65°C. | |
| (C) | Add solution from (B) slowly over 1 hour period to solution from (A), maintaining 60°C. temperature | |
| | Add sodium lauryl sulfate | 1.00 g |
| | Dissolve. Add- | |
| | 30% silicone emulsion | 1.00 g |
| | Mix well. | |
| (D) | In separate suitable container place- | |
| | Water purified | 550.00 ml |
| | Methylparaben | 1.60 g |
| | Mix well. Heat to 60°C. to dissolve. Add- | |
| | Microcrystalline cellulose 89% with sodium carboxymethylcellulose 11% | 40.00 g |
| | Mix well at 60°C. for 30 minutes, let stand overnight. | |

(E) Mix reaction mixture from (D) well and add to (C).
Add-
Sucrose, granulated  800.00 g
Xanthate gum  4.00 g
Mix well. Add-
F D and C Yellow No. 5  0.006 g
F D and C Red No. 40  0.06 g
Mixed fruit imitation flavor blend  0.60 ml
Mix well. Add water purified q.s. to 2000 ml.
Put mixture through homogenizer at 1500 PSI, mix well.

The suspension prepared in Example 6 above, is a very fine suspension requiring no grinding for the particles to pass 200 mesh. Further, the suspension has improved bioavailability because it dissolves easily in the stomach of the subject. The suspension is compatible with other pharmaceutical preparations placed in the suspension because the aluminum is highly insoluble and as such is inert to other potential reactants.

What is claimed is:

1. A compound of the formula:

wherein:
$n$ is 1 or 2; and
$R_1$ is the moiety

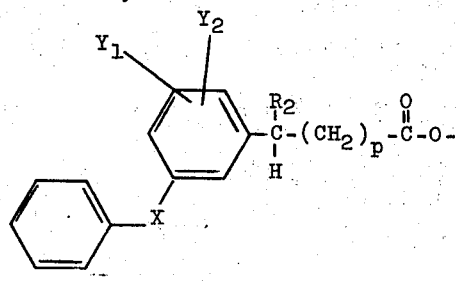

wherein:
$p$ is 0, 1, 2, or 3;
X is oxygen or sulfur;
$R_2$ is hydrogen, $C_1$-$C_5$ alkyl, $C_2$-$C_5$ alkenyl, $C_2$-$C_5$ alkynyl, or $C_3$-$C_6$ cycloalkyl; and
$Y_1$ and $Y_2$ are, independently, hydrogen, hydroxy, halo, $C_1$-$C_3$ alkyl, or $C_1$-$C_3$ alkoxy, but $Y_2$ is hydrogen when $Y_1$ is hydroxy or $C_1$-$C_3$ alkoxy.

2. A compound according to claim 1, said compound being di-[2-(3-phenoxyphenyl)propionoxy] aluminum hydroxide.

3. A compound according to claim 1, said compound being di-[2-(3-phenoxyphenyl)acetoxy] aluminum hydroxide.

4. A compound according to claim 1, said compound being 2-(3-phenoxyphenyl)propionoxy aluminum dihydroxide.

5. A compound according to claim 1, said compound being 2-(3-phenoxyphenyl)acetoxy aluminum dihydroxide.

* * * * *